United States Patent [19]

Kompis et al.

[11] 4,039,543
[45] Aug. 2, 1977

[54] BENZYLPYRIMIDINES

[75] Inventors: Ivan Kompis, Oberwil; Gerald Rey-Bellet, Basel; Guido Zanetti, Fullinsdorf, all of Switzerland

[73] Assignee: Hoffmann-La Roche Inc., Nutley, N.J.

[21] Appl. No.: 642,303

[22] Filed: Dec. 19, 1975

[30] Foreign Application Priority Data

Dec. 24, 1974 Switzerland .......... 17287/74
Oct. 27, 1975 Switzerland .......... 13883/75

[51] Int. Cl.$^2$ .......... C07D 239/48
[52] U.S. Cl. .......... 260/256.4 N; 424/251; 544/122; 544/123
[58] Field of Search .......... 260/256.4 N, 247.5 D

[56] References Cited

U.S. PATENT DOCUMENTS 3,822,264  7/1974  Roth .......... 260/256.4 N
3,931,181  1/1976  Kompis et al. .......... 260/256.4 N Primary Examiner—Paul M. Coughlan, Jr.
Attorney, Agent, or Firm—Samuel L. Welt; George M. Gould; William G. Isgro

[57] ABSTRACT

Benzylpyrimidines of the formula

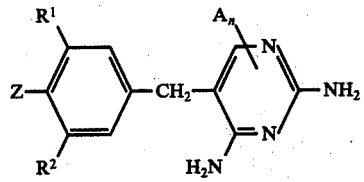

I wherein $R^1$ and $R^2$ each, independently, is amino, optionally $C_{1-3}$-alkyl-substituted pyrrolo, pyrrolidino, piperidino, -NHR$^3$, -N(R$^3$)$_2$, -NHR$^4$, -N(R$^3$)(R$^4$),-NR$^3$COOR$^3$, -NHCOOR$^3$, -NHCONHR$^3$, -NHCONH$_2$ or -N(NO)R$^3$ or wherein $R^3$ is $C_{1-4}$-alkyl or $C_{2-4}$-alkenyl, $R^4$ is acyl; Z is hydrogen, chlorine, bromine, pyrrolo, pyrrolidino, piperidino or morpholino or R$^3$, OR$^3$ or -N(R$^3$)$_2$; A is an oxygen atom bonded to one of the cyclic nitrogen atoms; and n is 0 or 1 are prepared. The benzylpyrimidines are useful as potentiators of the activity of the sulfonamides.

21 Claims, No Drawings

BENZYLPYRIMIDINES

BRIEF SUMMARY OF THE INVENTION

The invention relates to compounds of the formula

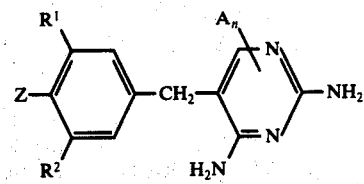

I wherein $R^1$ and $R^2$ each, independently, is amino, optionally $C_{1-3}$-alkyl-substituted pyrrolo, pyrrolidino, piperidino, -$NHR^3$, -$N(R^3)_2$, $NHR^4$, -$N(R^3)(R^4)$, -$NR^3COOR^3$, -$NHCOOR^3$, -$NHCONHR^3$, -$NHCONH_2$ or -$N(NO)R^3$ or wherein $R^3$ is $C_{1-4}$-alkyl or $C_{2-4}$-alkenyl, $R^4$ is acyl; Z is hydrogen, chlorine, bromine, pyrrolo, pyrrolidino, piperidino or morpholino or $R^3$, $OR^3$ or -$N(R^3)_2$; A is an oxygen atom bonded to one of the cyclic nitrogen atoms; and n is 0 or 1,
and pharmaceutically acceptable acid addition salts thereof. In another aspect, the invention relates to novel intermediates.

DETAILED DESCRIPTION OF THE INVENTION

The benzylpyrimidine derivatives provided by the present invention are compounds of the formula

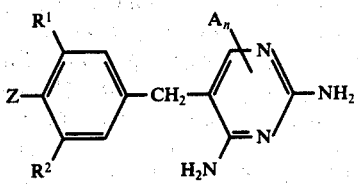

I wherein $R^1$ and $R^2$ each, independently, is amino, pyrrolo, pyrrolidino, piperidino, $C_{1-3}$alkyl-substituted pyrrolo, $C_{1-3}$-alkyl-substituted pyrrolidino, $C_{1-3}$-alkyl-substituted piperidino, -$NHR^3$, -$N(R^3)_2$, -$NHR^4$, -$N(R^3)(R^4)$, -$NR^3COOR^3$, -$NHCOOR^3$, -$NHCONHR^3$, -$NHCONH_2$ or -$N(NO)R^3$, wherein $R^3$ is $C_{1-4}$-alkyl or $C_{2-4}$-alkenyl, $R^4$ is acyl; Z is hydrogen, chlorine, bromine, pyrrolo, pyrrolidino, piperidino or morpholino or $R^3$, $OR^3$ or -$N(R^3)_2$; A is an oxygen atom bonded to one of the cyclic nitrogen atoms; and n is 0 or 1,
and pharmaceutically acceptable acid addition salts thereof.

The terms "$C_{1-4}$" and "$C_{2-4}$" used in this specification denote that the groups prefixed therewith contain 1-4 or 2-4 carbon atoms. The alkyl, alkoxy, alkenyl and alkenyloxy groups can be straight-chain or branched chain and expediently contain a low number of carbon atoms. Examples of such groups are methyl, ethyl, propyl, isopropyl and tert. butyl, methoxy, ethoxy, propoxy and isopropoxy, vinyl and allyl, and vinyloxy and allyloxy. The acyl groups are preferably derived from lower aliphatic carboxylic acids or sulfonic acids. The preferred acyl groups are derived from $C_{1-4}$-aliphatic monocarboxylic acids (e.g., formyl, acetyl, propionyl, butyryl and ethoxyacetyl) and from aliphatic sulfonic acids (e.g., mesyl).

A preferred group of compounds of formula I hereinbefore comprises those in which $R^1$ and $R^2$ each, independently, represent amino, pyrrolo, pyrrolidino, -$NHR^3$ or -$N(R^3)_2$, $R^3$ is $C_{1-4}$-alkyl or $C_{2-4}$-alkenyl and Z is chlorine or bromine or the group $R^3$ or $OR^3$. Furthermore, compounds of formula I in which n is 0 are preferred. Particularly preferred compounds are 2,4-diamino-5-[4-chloro-3,5-bis-(dimethylamino)benyzyl]-pyrimidine and 2,4-diamino-5-(4-chloro-3-dimethylamino-5-methylaminobenzyl)-pyrimidine.

Accordng to the process provided by the present invention, the benzylpyrimidine derivatives aforesaid (i.e., the compounds of formula I and their salts) are prepared by:

a. reacting a compound of the formula

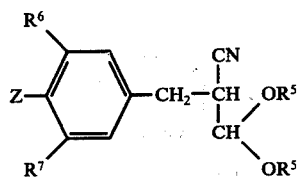

IIa or

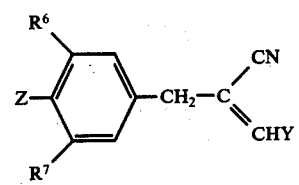

IIb wherein $R^6$ and $R^7$ each, independently, is amino, optionally $C_{1-3}$-alkyl-substituted pyrrolo, pyrrolidino, piperidino, -$NHR^3$, -$N(R^3)_2$, -$NHR^4$, -$N(R^3)(R^4)$, -$NR^3COOR^3$, -$NHCONH_2$, -$NHCOOR^3$ or -$NHCONHR^3$, $R^5$ is lower alkyl or both $R^5$'s together are lower alkylene, Y is a leaving group and $R^3$, $R^4$ and Z are as previously described,
wih guanidine, or b. reacting a compound of the formula

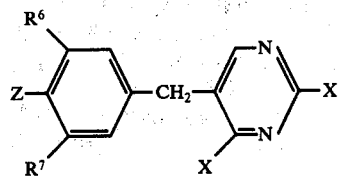

III wherein X is chlorine, bromine, alkylmercapto, alkylsulfonyl or amino, with the proviso that at least one X is other than amino, and Z, $R^6$ and $R^7$ are as previously described, or c. reductively removing the substituent denoted by $X^1$ in a compound of the formula

IV

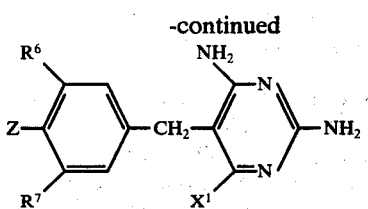

wherein $X^1$ is chlorine, bromine or hydroxy and $R^6$, $R^7$ and Z are as previously described, or d. treating a compound of formula I in which $R^1$ is $-NHR^3$ and $R^2$ has the foregoing significance with the exception of amino and Z, A and $n$ are as previously described, with nitrous acid, or e. converting the group denoted by $R^8$ and/or $R^{10}$ as the case may be in a compound of the formula

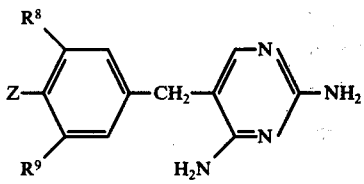

Va

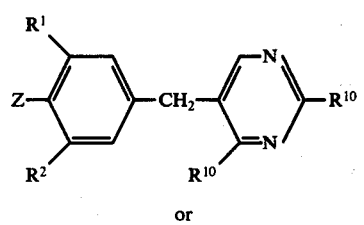

Vb or

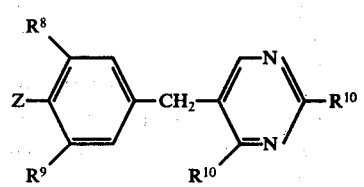

Vc wherein $R^1$ and $R^2$ are as previously described, $R^8$ is a group convertible by reaction or hydrolysis into an amino group or $-NHR^3$, $R^9$ is amino, pyrrolo, pyrrolidino, piperidino, $-NHR^3$, $-N(R^3)_2$ or $R^8$ and $R^{10}$, which can be the same or different in formulas Vb and Vc, are a group convertible into the amino group, into the amino group or $-NHR^3$, or f. alkylating or alkenylating the group(s)-$NHR^4$ or $-NHCOOR^3$ in a compound of the formula

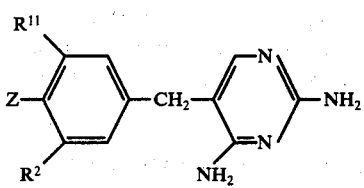

Ia wherein $R^{11}$ is $-NHR^4$ or $-NHCOOR^3$ and Z, $R^2$, $R^3$ and $R^4$ are as previously described, or g. subjecting a compound of the formula

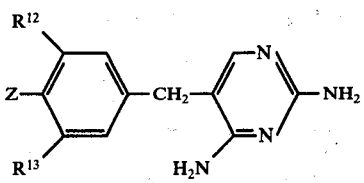

VI wherein $R^{12}$ and $R^{13}$ each, individually, is amino, pyrrolo, $-NHR^3$, $-NHR^4$, $-N(R^3)$ $(R^4)$, $-NR^3COOR^3$, $-NHCOOR^3$, $-NHCONHR^3$, $-NHCONH_2$ or $-N(NO)R^3$ and $Z^1$ is hydrogen, chlorine, bromine or pyrrolo or a group $R^3$ or $OR^3$; and $R^3$ and $R^4$ are as previously described, to N-oxidation, and, if desired, converting a compound of formula I obtained into a salt.

According to process embodiment (a), a compound of formula IIa or IIb is reacted with guanidine. The symbol Y in a compound of formula IIb is a leaving group. Examples of such leaving groups are ether groups, e.g., lower alkoxy groups such as methoxy and ethoxy, thioether groups, e.g., lower alkylthio groups, or amino groups derived from primary or secondary amines. Examples of such amino groups are i) groups derived from primary aliphatic, aryl-aliphatic or aromatic amines such as lower alkylamino, benzylamino and arylamino, e.g., naphthylamino, but especially phenylamino (anilino) which may carry in the phenyl ring one or more halogen, lower alkyl or lower akoxy substituents, or ii) groups derived from secondary aliphatic, aromatic or heterocyclic amines such aS N,N-di(lower alkyl)amino, N-(lower alkyl)-N-arylamino, e.g., N-methyl-N-phenylamino (N-methylanilino) which may carry in the phenyl ring one or more halogen, lower alkyl or lower alkoxy substituents, pyrrolidino, piperidino, piperazino and morpholino. An especially preferred amino leaving group is anilino.

The reaction of a compound of formula IIa or IIb with guanidine can be carried out according to methods known per se, for example, as described in Belgian Patent Specifications Nos. 595,131; 671,982 and 746,846. For example, the reaction can be carried out in a solvent such as alkanol, e.g., methanol or ethanol, dimethylformamide, dimethylsulfoxide or N-methyl-pyrazolone at a temperature in the approximate range of from 25° C to 200° C., preferably at 50° C. to 170° C.

The compounds of formula IIb can be formed in situ under the conditions of the reaction from the tautomeric compound of the formula

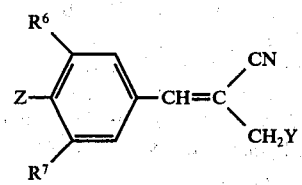

IIc wherein $R^6$, $R^7$, Z and Y are as previously described. The compounds of formulas IIb and IIc can occur as cis or trans isomers or as mixtures thereof. Embodiment (a) of the present process leads to compounds of formula I in which $n$ is 0, $R^1$ and $R^2$ each are a group $R^6$ or $R^7$ and $Z$ is as previously described.

According to process embodiment (b), a compound of formula III is reacted with ammonia, the bromine or chlorine atom or the alkylmercapto or alkylsulfonyl group present in the pyrimidine nucleus being replaced by an amino group. The reaction is expediently carried out in an alkanolic solution, especially a methanolic solution (e.g. methanolic ammonia is uses as the reaction partner). The reaction is expediently carried out at a temperature between about 80° C. and 200° C., especially at a temperature between about 100° C. and 150° C. Since these temperatures lie above the boiling point of methanol, the reaction is then carried out in a closed system, e.g., in an autoclave.

Embodiment (b) of the present process leads to compounds of formula I in which $n$ is 0, $R^1$ and $R^2$ each are a group $R^6$ or $R^7$ and $Z$ is as previously described.

The removal of a bromine or chlorine atom from a compound of formula IV in accordance with process embodiment (c) can be carried out by treatment with a reducing agent such as hydrogen ioside or catalytically activated hydrogen, e.g., palladium in alcohol, or with zinc/glacial acetic acid or amalgamated zinc/sodium hydroxide. When $X^1$ is hydroxy, the compound of formula IV is reacted, for example, with 1-phenyl-5-chlorotetrazole and the resulting 1-phenyltetrazol-5-yl ether is hydrogenated over palladium/carbon. Alternatively, the compound of formula IV is first reacted with cyanogen bromide in the presence of triethylamine and the reaction product is hydrogenated over palladium/carbon.

Embodiment (c) of the present process provides compounds of formula I in which $n$ is 0, $R^1$ and $R^2$ each is a group $R^6$ or $R^7$, and $Z$ is as previously described.

Process embodiment (d) can be carrid out in a known manner by means of nitrous acid or nitrite and acid. As a solvent for this reaction there may be mentioned aqueous hydrochloric acid.

Embodiment (d) of the present process yields compounds of formula I in which $R^1$ and/or $R^2$ are -N(NO)$R^3$ and $Z$, $A$ and $n$ are as previously described.

The carbobenzoxyamino group is an example of a group denoted by $R^8$ or $R^{10}$ which is converted by reduction into an amino group according to process embodiment (e). The reductive conversion of such groups into an amino group can be carried out by catalytic hydrogenation, for example, by means of hydrogen and palladium on carbon in an alcohol, e.g., methanol, at 10°–50° C., preferably at room temperature.

Groups denoted by $R^8$ and $R^{10}$ which are convertible by hydrolysis into an amino group or into the group -NHR$^3$ are, for example, -NHR$^4$, -N=CHR, -N=C(R)$_2$, -N=CHOR$^3$, -NHCOOR$^3$, -NR$^3$COOR$^3$ and -N(R$^3$)(R$^4$) (R is alkyl, alkenyl or aryl and R$^3$ and R$^4$ are as previously described) and phthalimido. The hydrolysis of these groups is expediently carried out in an acidic medium, e.g., with aqueous or aqueous-alcoholic mineral acids such as hydrochloric acid. Groups which can be hydrolyzed under alkaline conditions are -NR$^3$COOR$^3$, -NH-COOR$^3$ and -NHCHO. The alkaline hydrolysis can be carried out with aqueous or aqueous-alcoholic (methanolic) alkali. The phthalimido group can preferably be converted into the amino group by hydrazinolysis.

The groups denoted by $R^{10}$ are expediently hydrolyzable groups such as acetylamino or formylamino, phthalimido or carbobenzoxyamino.

Embodiment (e) of the present process leads to compounds of formula I in which $n$ 0, $R^1$ is amino or -NHR$^3$, R$^2$ is amino, pyrrolo, pyrrolidino, piperidino, NHR$^3$ or N(R$^3$)$_2$ and $Z$ and $R^3$ are as previously described.

The alkylation or alkenylation according to process embodiment (f) can be carried out using and alkyl halide, e.g., methyl iodide, or an alkenyl halide, e.g., allyl bromide, in the presence of a base, e.g., sodium methylate or sodium hydride. As the solvent, there can be used, for example, dimethylformamide or dimethylsulfoxide.

Embodiment (f) of the present process leads to compounds of formula I in which $n$ is 0, $R^1$ is -N(R$^3$) (R$^4$) or -NR$^3$COOR$^3$, and $Z$, $R^2$, $R^3$ and $R^4$ are as previously described.

The N-oxidation according to embodiment (g) of the present process can be carried out according to methods known per se using a customary N-oxidation agent. Especially preferred N-oxidation agents are perbenzoic acid, particularly m-chlorperbenzoic acid. The N-oxidation can be carried out, for example, in an inert solvent such as a chlorinated hydrocarbon, e.g., chloroform or methylene chloride, an alcohol, e.g., methanol or ethanol, dimethylformamide, dimethylsulfoxide, water or dioxane. The N-oxidation is expediently carried out at a temperature between room temperature and the boiling point of the solvent, expediently at a temperature between about 10° C. and about 60° C. A temperature between about 10° C. and about 20° C. is preferred.

An N-oxide obtained can be isolated from the oxidation mixture in the usual manner. When m-chloroperbenzoic acid or perbenzoic acid is used as the N-oxidation agent, it has been found to be expedient to extract the oxidation solution with as weakly aqueous-alkaline solution, e.g., aqueous sodium bicarbonate solution, to acidify the aqueous extract obtained in order to precipitate the excess acid and, after removal of the excess acid by filtration, to make the filtrate neutral or slightly basic.

The N-oxidation normally leads to mixtures of $N_1$- and $N_3$-oxides of the formulas

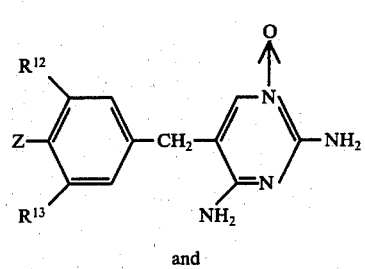

Ib and

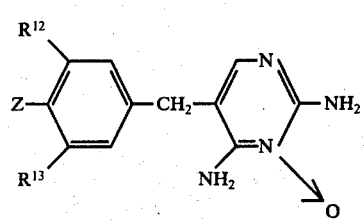

Ic wherein $R_{12}$ and $R^{13}$ are as previously described.

The separation and purification of the foregoing isomeric N-oxidation products can be carried out by chromatography, e.g., column chromatography, and/or recrystallization, preferably from polar solvents such as alcohols, water, etc.

The starting materials used in the present process insofar as they are not known or insofar as they are not described hereinafter, can be prepared in a manner analogous to that described in the Examples hereinafter or according to the methods given in the following Table in which R, $R^6$, $R^7$, Y and Z are as previously described.

syrup can contain (per 5 ml.) 40 mg. of a compound of formula I and 200 mg. of sulfamethoxazole.

The compounds of formula I possess a high antibacterial activity and a pronounced synergistic effect in combination with sulfonamides. They also have a good compatibility.

The following Examples further illustrate the invention. All temperatures are stated in degrees Centigrade, unless otherwise stated.

TABLE

| Starting material | Prepared from | Reaction | Literature |
|---|---|---|---|
| IIb IIc | $R^6$-substituted Z-phenyl-CHO + CH$_2$(CN)(CH$_2$Y), $R^7$ | Condensation in strongly alkaline medium | Belgian Patent Specifications Nos. 594 131, 746 846 |
| IIa III | IIb: $R^6$-substituted Z-phenyl-CH$_2$-pyrimidine with NH$_2$(OH), HO, $R^7$ | Alcohol addition Halogenation, if desired followed by reaction with mercaptans and alkali | Belgian Patent Specification No. 565 002 |
| IV | $R^6$-substituted Z-phenyl-CH$_2$CH(CN)(COOR), $R^7$ | 1) Condensation with guanidine in alkaline medium 2) Replacement of the hydroxy group by a bromine or chlorine atom using a phosphorus halide or phosphorus oxyhalide | DOS 2003578 |

The compounds of formula I can be converted into acid addition salts, especially those which are customary in pharmaceutical preparations, by treatment with inorganic acids, e.g., hydrochloric acid, sulfuric acid, phosphoric acid, etc., or organic acids, e.g., formic acid, acetic acid, succinic acid, lactic acid, citric acid, maleic acid, fumaric acid, tartaric acid, methanesulfonic acid, p-toluenesulfonic acid, etc.

The benzylpyrimidine derivatives provided by this invention, i.e., the compounds of formula I and their salts, possess antibacterial activity. They inhibit the bacterial dihydrofolate reductase and potentiate the antibacterial action of sulfonamides such as, for example, sulfisoxazole, sulfadimethoxine, sulfamethoxazole, 4-sulfanilamido-5,6-dimethoxy-pyrimidine, 2-sulfanilamido-4,5-dimethyl-pyrimidine, sulfaquinoxaline, sulfadiazine, sulfamonomethoxine, 2-sulfanilamido-4,5-dimethyl-isoxazole and other inhibitors of enzymes which are involved in the folic acid biosynthesis such as, for example, pteridine derivatives.

A combination of one or more of the present benzylpyrimidine derivatives with sulfonamides can be used in human medicine in a form adapted for oral, rectal or parenteral administration. The ratio of a compound of formula I to a sulfonamide can vary within a wide range, for example, between 1:40 parts by weight and 5:1 parts by weight, the preferred ratio being between 1:1 to 1:5.

Thus, for example, a tablet can contain 80 mg. of a compound of formula I and 400 mg. of sulfamethoxazole, another tablet can contain 20 mg. of a compound of formula I and 100 mg. of sulfamethoxazole and a

EXAMPLE 1

Preparation of 2,4-diamino-5-[3,5-bis(dimethylamino-4-methylbenzyl]-pyrimidine

A solution of 1.5 g. of sodium in 100 ml. of absolute ethanol was treated with 6.33 g. of guanidine hydrochloride and 7.35 g. of α-(anilinomethylene)-3,5-bis(-dimethylamino)-4-methylhydrocinnamic acid nitrile and boiled under reflux for 20 hours. The mixture was diluted with 180 ml. of water and the ethanol removed in vacuo. The precipitated 2,4-diamino-5-[3,5-bis(dimethylamino)-4-methylbenzyl]-pyrimidine was filtered off under suction, washed with water and recrystallized from ethanol; melting point 191°-192° C.

The starting material was prepared as follows:

A mixture of 27 g. of methyl 3,5-diamino-4-methylbenzoate, 75.6 g. of dimethylsulfate, 207 g. of dry potassium carbonate and 1000 ml. of acetone was boiled under reflux for 20 hours with stirring. After cooling, the inorganic salts were filtered off from the solution, the acetone removed in vacuo, the residue treated with 2000 ml. of water, the precipitated oil extracted twice with 200 ml. of ethyl acetate each time, the ethyl acetate solution washed with water, dried over sodium sulfate and evaporated. There was obtained an oil from which methyl 3,5-bis(dimethylamino)-4-methylbenzoate was isolated as an oil by column chromatography over silica gel with methylene chloride/ethyl acetate (9:1). The hydrochloride melted at 216° C. (from ethanol/ether).

A suspension of 18.8 g. of dimethylsulfone and 3.6 g. of sodium hydride (50% dispersion in oil) in 80 ml. of dimethylsulfoxide was stirred with the exclusion of moisture for 2 hours at 50° C. Thereupon, 23.6 g. of methyl 3,5-bis(dimethylamino)-4-methylbenzoate were added and the mixture was stirred at room temperature for 1.5 hours. The solution was diluted with 400 ml. of water and extracted twice with ethyl acetate. The ethyl acetate phases were combined, washed with water, dried over sodium sulfate and evaporated to dryness in vacuo. After recrystallization of the residue from methanol, there was obtained 3′,5′-bis(dimethylamino)-4′-methyl-2-methylsulfonylacetophenone, having a melting point of 161°–163° C.

A suspension of 4.75 g. of 3′,5′-bis(dimethylamino)-4′-methyl-2-methylsulfonylacetophenone and 0.20 g. of sodium borohydride in 200 ml. of ethanol was stirred at room temperature for 2 hours. The solution was diluted with 100 ml. of water, cooled, the precipitated 3,5-bis(dimethylamino)-4-methyl-α-[(methylsulfonyl)methyl]-benzyl alcohol was filtered off under suction and recrystallized from ethanol; methanol point 163°–164° C.

A mixture of 1.8 g. of sodium methylate, 4.8 g. of β-anilinopropionitrile and 9.0 g. of 3,5-bis(dimethylamino)-4-methyl-α-[(methylsulfonyl)methyl]benzyl alcohol in 20 ml. of dimethylsulfoxide was stirred with the exclusion of moisture for 5 hours at 40° C. The mixture was poured into 250 ml. of water and the resulting emulsion extracted three times with 300 ml. of ethyl acetate. The ethyl acetate phases were combined, washed with water, dried over sodium sulfate and evaporated. The residue, α-(anilinomethylene)-3,5-bis(dimethylamino)-4-methylhydrocinnamic acid nitrile, was recrystallized from methanol and melted at 151°–152° C.

EXAMPLE 2

Preparation of
5′-[(2,4-diamino-5-pyrimidinyl)methyl]-3′-dimethylamino-2′-methoxy-N-methylacetanilide A solution of 1.7 g. of sodium in 110 ml. of absolute ethanol was treated with 7.04 g. of guanidine hydrochloride and 9.2 g. of 5′-(3-anilino-2-cyanoallyl)-3′-dimethylamino-2′-methoxy-N-methylacetanilide and boiled under reflux for 20 hours. The alcohol was removed in vacuo, the residue taken up in water, the solid material filtered off under suction and recrystallized from ethanol. The 5′-[(2,4-diamino-5-pyrimidinyl)methyl]-3′-dimethylamino-2′-methoxy-N-methylacetanilide melted at 220°–222° C.

The starting material was prepared as follows:

A mixture of 29.4 g. of methyl 3,5-diamino-4-methoxybenzoate, 57.3 ml. of dimethylsulfate, 207 g. of dry potassium carbonate and 1000 ml. of acetone was boiled under reflux for 16 hours with stirring. After cooling, inorganic salts were filtered from the solution, the acetone was removed in vacuo, the residue treated with 200 ml. of water, the precipitated oil extracted twice with 300 ml. of ethyl acetate each time, the ethyl acetate solution washed with water, dried over sodium sulfate and evaporated. There was obtained an oil from which methyl 3-dimethylamino-5-methylamino-p-anisoate and methyl 3,5-bis(dimethylamino)-p-anisoate were isolated by column chromatography over silica gel with methylene chloride/ethyl acetate (9:1).

25 G. of methyl 3-dimethylamino-5-methylamino-p-anisoate and 100 ml. of acetic anhydride were heated on a steam bath for 1 hour. The excess anhydride was removed in vacuo and the residue recrystallized from high-boiling petroleum ether. The methyl 3-dimethylamino-5-(N-methylacetamido)-p-anisoate melted at 88°–89° C.

A suspension of 7.05 g. of dimethylsulfone and 2.4 g. of sodium hydride (50% dispersion in oil) in 18 ml. of dimethylsulfoxide was stirred with the exclusion of moisture for 2 hours at 50° C. Thereupon, 6.95 g. of methyl 3-dimethylamino-5-(N-methylacetamido)-p-anisoate were added and the mixture was stirred for 1 hour at room temperature. The solution was diluted with 100 ml. of water, made acidic with acetic acid and extracted twice with ethyl acetate. The ethyl acetate phases were combined, washed with water, dried over sodium sulfate and evaporated to dryness in vacuo. After recrystalization of the residue from methanol, the 3′-dimethylamino-2′-methoxy-N-methyl-5′-[(methylsulfonyl)acetyl]acetanilide melted at 174°–176° C.

A suspension of 10.9 g. of 3′-dimethylamino-2′-methoxy-N-methyl-5′-[(methylsulfonyl)acetyl]acetanilide and 0.40 g. of sodium borohydride in 50 ml. of 85% aqueous ethanol was stirred for 1.5 hours at 20° C., made neutral with acetic acid and concentrated in vacuo. The precipitated oil was extracted with ethyl acetate, the ethy acetate solution evaporated and the residue recrystallized from ethyl acetate/petroleum ether. The 3′-dimethylamino-5′-[1-hydroxy-2-(methylsulfonyl)ethyl]-2′-methoxy-N-methylacetanilide melted at 118°–119° C.

A mixture of 10.6 g. of 3′-dimethylamino-5′-[1-hydroxy-2-(methylsulfonyl)-ethyl]-2′-methoxy-N-methylacetanilide, 1.8 g. of sodium methylate and 4.8 g. of β-anilinopropionitrile in 20 ml. of dimethylsulfoxide was stirred with the exculsion of moisture for 5 hours at 50° C. The mixture was poured into 250 ml. of water, the precipitated oil extracted with ethyl acetate, the ethyl acetate solution dried over sodium sulfate and evaporated. By purification of the residue over aluminum oxide with benzene and recrystallization from ethyl acetate/petroleum ether, there was obtained the 5′-(3-anilino-2-cyanoallyl)-3′-dimethylamino-2′-methoxy-N-methylacetanilide, having a melting point of 176°–178° C.

EXAMPLE 3

Preparation of
2,4-diamino-5-[3-dimethylamino-4-methoxy-5-(methylamino)benzyl]-pyrimidine 4.0 G. of 5′-[(2,4-diamino-5-pyrimidinyl)methyl]3′-dimethylamino-2′-methoxy-N-methylacetanilide (prepared as described in the first paragraph of Example 2) and 100 ml. of 1-N hydrochloric acid were boiled under reflux for 2 hours. After neutralization and evaporation in vacuo, purification of the residue over silica gel with methylene chloride/propanol (8:2) and recrystallization from ethanol, there was obtained 2,4-diamino-5-[3-dimethylamino-4-methoxy-5-(methylamino)benzyl]-pyrimidine, having a melting point of 183° C.

EXAMPLE 4

Preparation of
2,4-diamino-5-[3,5-bis-(dimethylamino)-4-methoxybenzyl]-pyrimidine A solution of 1.7 g. of sodium in 110 ml. of absolute ethanol was treated with 7.04 g. of guanidine hydrochloride and 8.5 g. of α-(anilinomethylene)-3,5-bis(- dimethylamino)-4-methoxyhydrocinnamonitrile and boiled under reflux for 20 hours. The alcohol was removed in vacuo, the residue taken up in water, the solid material filtered off under suction and recrystallized from ethanol. The 2,4-diamino-5-[3,5-bis-(dimethylamino)-4-methoxybenzyl]pyrimidine melted at 207°–208° C.

The starting material was prepared as follows:

A suspension of 3.6 g. of sodium hydride (50% dispersion in oil) and 9.4 g. of dimethylsulfone in 40 ml. of dimethylsulfoxide was stirred with the exclusion of moisture for 2 hours at 50° C. Thereupon, 12.6 g. of methyl 3,5-bis(dimethylamino)-p-anisoate (obtained as described in Example 2) were added, and the mixture was for 2 hours at room temperature. The solution was diluted with 200 ml. of water, extracted with ethyl acetate, the ethyl acetate solution washed with water, dried over sodium sulfate and evaporated. After recrystallization of the residue from ethyl acetate/petroleum ether, the 3',5'-bis(dimethylamino)-4'-methoxy-2-methylsulfonylacetophenone melted at 103°–104° C.

A suspension of 5.04 g. of 3',5'-bis(dimethylamino)-4'-methoxy-2-methylsulfonylacetophenone and 0.20 g. of sodium borohydride in 10 ml. of 70% aqueous ethanol was stirred at room temperature for 1.5 hours, cooled, the solid material filtered off under suction and recrystallized from methanol. The 3,5-bis(dimethylamino)-4-methoxy-$\alpha$-[(methylsulfonyl)-methyl]benzyl alcohol melted at 161°–162° C.

A mixture of 9.76 g. of 3,5-bis(dimethylamino)-4-methoxy-$\alpha$-[(methylsulfonyl)methyl]benzyl alcohol, 1.8 g. of sodium methylate and 4.8 g. of $\beta$-anilinopropionitrile in 20 ml. of dimethylsulfoxide was stirred with the exclusion of moisture for 5 hours at 50° C. The mixture was poured into 250 ml. of water the precipitated oil extracted with ethyl acetate, the ethyl acetate solution dried over sodium sulfate and evaporated. By recrystallization of the residue from high-boiling petroleum ether, there was obtained $\alpha$-(anilinomethylene)-3,5-bis(-dimethylamino)-4-methoxyhydrocinnamonitrile, having a melting point of 103°–105° C.

EXAMPLE 5

Preparation of
2,4-diamino-5-[4-chloro-3,5-bis(dimethylamino)benzyl]-pyrimidine

A solution of 1.7 g. of sodium in 110 ml. of absolute ethanol was treated with 7.04 g. of guanidine hydrochloride and 8.6 g. of $\alpha$-(anilinomethylene)-4-chloro-3,5-bis(dimethylamino)hydrocinnamonitrile and boiled under reflux for 20 hours. The ethanol was removed in vacuo, the residue taken up in water, filtered off under suction and recrystallized from ethanol. The 2,4-diamino-5-[4-chloro-3,5-bis(dimethylamino)benzyl]-pyrimidine melted at 202°–203° C.

The starting material was prepared as follows:

A mixture of 22.5 g. of methyl 3,5-diamino-4-chlorobenzoate, 50 ml. of dimethylsulfate, 155 g. of dry potassium carbonate and 750 ml. of acetone was boiled under reflux for 16 hours with stirring. After cooling, the inorganic salts were filtered off, the acetone removed in vacuo, the residue taken up in ethyl acetate, the ethyl acetate solution washed with water, dried over sodium sulfate and evaporated. By column chromatography of the product over silica gel with methylene chloride/ethyl acetate (9:1), there were obtained methyl 4-chloro-3,5-bis(dimethylamino)benzoate, having a boiling point of 0.01/100° C. and methyl 4-chloro-3-dimethylamino-5-methylaminobenzoate, having a boiling point of 0.01/110° C.

A suspension of 7.05 g. of dimethylsulfone and 2.4 g. of sodium hydride (50% dispersion in oil) in 17 ml. of dimethylsulfoxide was stirred with the exclusion of moisture for 2 hours at 50° C. Thereupon, 6.35 g. of methyl 4-chloro-3,5-bis(dimethylamino)benzoate were added, and the mixture was stirred for 1.5 hours at 20° C. The solution was diluted with 200 ml. of water and extracted twice with ethyl acetate. The ethyl acetate phases were combined, washed with water, dried over sodium sulfate and evaporated in vacuo. After recrystallization of the residue from ethanol, the 4'-chloro-3',5'-bis(dimethylamino)-2-methylsulfonylacetophenone melted at 150° C.

A suspension of 25.45 g. of 4'-chloro-3',5'-bis(dimethylamino)-2-methylsulfonylacetophenone and 1.0 g. of sodium borohydride in 150 ml. of 20% aqueous ethanol was stirred for 2 hours at room temperature and then cooled with ice. The precipitate was filtered off under suction and recrystallized from ethanol. The 4-chloro-3,5-bis(dimethylamino)-$\alpha$-[(methylsulfonyl)methyl]benzyl alcohol melted at 168° C.

A mixture of 15.7 g. of 4-chloro-3,5-bis(dimethylamino)-$\alpha$-[(methylsulfonyl)methyl]benzyl alcohol, 2.8 g. of sodium methylate and 7.1 g. of $\beta$-anilinopropionitrile in 31 ml. of dimethylsulfoxide was stirred with the exclusion of moisture for 5 hours at 50° C. The mixture was poured into 200 ml. of water, the precipitated oil extracted with ethyl acetate, the ethyl acetate solution dried over sodium sulfate and evaporated in vacuo. By purification of the residue over aluminum oxide with benzene and recrystallization from ethyl actate/petroleum ether, there was obtained $\alpha$-(anilinomethylene)-4-chloro-3,5-bis(dimethylamino)hydrocinnamonitrile, having a melting point of 168° C.

EXAMPLE 6

Preparation of
2,4-diamino-5-[4-chloro-3-dimethylamino-5-methylaminobenzyl]-pyrimidine A solution of 0.9 g. of sodium in 60 ml. of absolute ethanol was treated with 3.7 g. of guanidine hydrochloride and 4.3 g. of $\alpha$-(anilinomethylene)-4-chloro-3-dimethylamino-5-methylaminohydrocinnamonitrile and boiled under reflux for 20 hours. The alcohol was removed in vacuo, the residue taken up in water, filtered off under suction and recrystallized from ethanol. The 2,4-diamino-5-[4-chloro-3-dimethylamino-5-methylaminobenzyl]pyrimidine melted at 215°–216° C.

The starting material was prepared as follows:

A suspension of 2.4 g. of sodium hydride (50% dispersion in oil) and 7.05 g. of dimethylsulfone in 18 ml. of dimethylsulfoxide was stirred with the exclusion of moisture for 2 hours at 50° C. Thereupon, 5.77 g. of methyl 4-chloro-3-dimethylamino-5-methylaminobenzoate (obtained as described in Example 5) were added, and the mixture was stirred for 2 hours at room temperature. The solution was diluted with 100 ml. of water, the aqueous solution washed with ethyl acetate and made slightly acidic with ethyl acetate. After standing for 18 hours at 4° C., the precipitated 4-chloro-3-dimethylamino-5-methylamino-2-methylsulfonylacetophenone was filtered off under suction and recrystallized from ethanol; melting point 152° C.

A suspension of 4.85 g. of 4-chloro-3-dimethylamino-5-methylamino-2-methylsulfonylacetophenone and 0.20 g. of sodium borohydride in 30 ml. of 20% aqueous ethanol was stirred for 1 hour at 20° C., cooled with ice and the 4-chloro-3-dimethylamino-5-methylamino-α-[(methylsulfonyl)methyl]benzyl alcohol was filtered off under suction and recrystallized from ethanol; melting point 147°–148° C.

A mixture of 9.48 g. of 4-chloro-3-dimethylamino-5-methylamino-α-[(methylsulfonyl)methyl]benzyl alcohol, 1.8 g. of sodium methylate and 4.8 g. of β-anilinopropionitrile in 20 ml. of dimethylsulfoxide was stirred with the exclusion of moisture for 5 hours at 50° C. The mixture was cooled, poured into 200 ml. of water, the precipitated oil extracted with ethyl acetate, the ethyl acetate solution dried over sodium sulfate and evaporated. By purification of the product over aluminum oxide with benzene and recrystallization from ethanol, there was obtained α-(anilinomethylene)-4-chloro-3-dimethylamino-5-methylaminohydrocinnamonitrile, having a melting point of 173°–174° C.

EXAMPLE 7

Preparation of 2,4-diamino-5-[3,5-bis(2,5-dimethylpyrrol-1-yl)-4-methylbenzyl]-pyrimidine A solution of 0.53 g. of sodium in 36 ml. of absolute ethanol was treated with 2.16 g. of guanidine hydrochloride and 3.2 g. of α-(anilinomethylene)-3,5-bis(2,5-dimethylpyrrol-1-yl)-4-methylhydrocinnamonitrile and boiled under reflux for 20 hours. The alcohol was removed in vacuo, the residue taken up in water, filtered off under suction and recrystallized from methanol/water. The 2,4-diamino-5-[3,5-bis(2,5-dimethylpyrrol-1-yl)-4-methylbenzyl]pyrimidine melted at 205°–206° C.

The starting material was prepared as follows:

A mixture of 10.8 g. of methyl 3,5-diamino-4-methylbenzoate and 30 g. of acetonylacetone was heated under nitrogen at 200° C. for 17 hours. On the following day, the solid mass was dissolved in benzene, the benzene solution purified over aluminum oxide, evaporated, and the residue recrystallized from methanol. The methyl 3,5-bis(2,5-dimethylpyrrol-1-yl)-4-methylbenzoate melted at 163°–165° C.

A suspension of 6.25 g. of dimethylsulfone and 2.4 g. of sodium hydride (50% dispersion in oil) in 30 ml. of dimethylsulfoxide was stirred with the exclusion of moisture for 2 hours at 50° C. Thereupon, 11.2 g. of methyl 3,5-bis(2,5-dimethylpyrrol-1-yl)-4-methylbenzoate were added, and the mixture was stirred for 1.5 hours at 20° C. The solution was diluted with 150 ml. of water, the precipitated product extracted with ethyl acetate, the ethyl acetate solution dried over sodium sulfate and evaporated. 3′,5′-Bis(2,5-dimethylpyrrol-1-yl)-4′-methyl-2-methylsulfonylacetophenone, having a melting point of 173° C., was isolated from the residue by column chromatography over silica gel with methylene chloride/ethyl acetate (9:1).

A suspension of 1.9 g. of 3′,5′-bis(2,5-dimethylpyrrol-1-yl)-4′-methyl-2-methylsulfonylacetophenone and 0.40 g. of sodium borohydride in 50 ml. of 90% aqueous ethanol was stirred for 3 hours at room temperature, cooled, the precipiate filtered off under suction and recrystallized from ethanol. The 3,5-bis(2,5-dimethylpyrrol-1-yl)-4-methyl-α-[(methylsulfonyl)methyl]benzyl alcohol melted at 207°–208° C.

A mixture of 4.95 g. of 3,5-bis(2,5-dimethylpyrrol-1-yl)-4-methyl-α-[(methylsulfonyl)methyl]benzyl alcohol, 0.95 g. of sodium methylate and 2.16 g. of β-anilinopropionitrile in 13 ml. of dimethylsulfoxide was stirred with the exclusion of moisture for 5 hours at 50° C. The mixture was poured into 100 ml. of water, the precipitated oil extracted with ethyl acetate, the ethyl acetate solution dried over sodium sulfate and evaporated. By purification of the residue over aluminum oxide with ethyl acetate and recrystallization from ethyl acetate, there was obtained α-(anilinomethylene)-3,5-bis(2,5-dimethylpyrrol-1-yl)-4-methylhydrocinnamonitrile, having a melting point of 252° C.

EXAMPLE 8

Preparation of N-[α$^5$-(2,4-diamino-5-pyrimidinyl)-3-(pyrrol-1-yl)-2,5-xylyl]-acetamide A solution of 0.94 g. of sodium in 65 ml. of absolute ethanol was treated with 3.85 g. of guanidine hydrochloride and 6.6 g. of 5′-(3-anilino-2-cyanoallyl)-3′-(pyrrol-1-yl)-o-acetotoluidide and boiled for 20 hours under reflux and under nitrogen. The alcohol was removed in vacuo, the residue taken up in water, filtered off under suction and recrystallized from methanol. The N-[α$^5$-(2,4-diamino-5-pyrimidinyl)-3-(pyrrol-1-yl)-2,5-xylyl]acetamide melted at 110° C.

The starting material was prepared as follows:

A mixture of 18 g. of methyl 3,5-diamino-4-methylbenzoate, 0.7 g. of p-toluenesulfonic acid, 8.2 g. of sodium acetate, 32 g. of diethoxytetrahydrofuran, 10 ml of glacial acetic acid, 100 ml. of ethanol and 100 ml. of water was boiled at reflux for 3 hours. The alcohol was removed in vacuo and the residue extracted with ethyl acetate. The ethyl acetate solution was washed with water, dried over sodium sulfate and evaporated. By purification of the residue over aluminum oxide with ethyl acetate and recrystallization from high-boiling petroleum ether, there was obtained methyl 3-amino-4-methyl-5-(pyrrol-1-yl)benzoate, having a melting point of 112° C.

A suspension of 4.6 g. of methyl 3-amino-4-methyl-5-(pyrrol-1-yl)benzoate in 15 ml. of glacial acetic acid was treated with 2.1 g. of acetic anhydride. With self-heating, there resulted firstly a clear solution and soon afterwards crystals began to separate. The mixture was heated on a steam bath for a further 30 minutes and then cooled. The crystals were filtered off under suction and recrystallized from methanol. The methyl 3-acetamido-4-methyl-5-(pyrrol-1-yl)benzoate melted at 184°–185° C.

A suspension of 1.44 g. of sodium hydride (50% dispersion in oil) and 3.7 g. of dimethylsulfone in 20 ml. of dimethylsulfoxide was stirred with the exclusion of moisture for 2 hours at 50° C. Thereupon, 5.45 g. of methyl 3-acetamido-4-methyl-5-(pyrrol-1-yl)benzoate were added and the mixture was stirred for 2 hours at room temperature. The solution was diluted with 200 ml. of water, the aqueous solution washed with ethyl acetate, made slightly acidic with acetic acid and left to stand overnight in a refrigerator. On the following day, the precipitate was filtered off under suction and recrystallized from ethanol. The 5′-[(methylsulfonyl)acetyl]-3′-(pyrrol-1-yl)-o-acetotoluidide melted at 212°–214° C.

A suspension of 1.6 g. of 5′-[(methylsulfonyl)acetyl]-3′-(pyrrol-1-yl)-o-acetotoluidide and 0.40 g. of sodium borohydride in 50 ml. of 50% aqueous ethanol was stirred at room temperature for 30 minutes. The ethanol was removed in vacuo, the precipitate filtered off under suction, dried and recrystallized from ethyl acetate/petroleum ether. The 5′-[1-hydroxy-(2-methylsulfonyl)e- thyl]-3'-(pyrrol-1-yl)-o-acetotoluidide melted at 167°-168° C.

A mixture of 1.35 g. of 5'-[1-hydroxy-2-(methylsulfonyl)ethyl]-3'-(pyrrol-1-yl)-o-acetotoluidide, 0.43 g. of sodium methylate and 1.1 g. of β-anilinopropionitrile in 12 ml. of dimethylsulfoxide was stirred with the exclusion of moisture for 1 hour at room temperature. The mixture was poured into 100 ml. of water, the precipitated oil extracted with ethyl acetate, the ethyl acetate solution washed with water, dried over sodium sulfate and evaporated. By column chromatography over silica gel with methylene chloride/ethyl acetate (9:1) and recrystallization from ethanol, there was obtained 5'-(3-anilino-2-cyanoallyl)-3'-(pyrrol-1-yl)-o-acetotoluidide, having a melting point of 218°-220° C.

EXAMPLE 9

Preparation of 2,4-diamino-5-[3-amino-4-methyl-5-(pyrrol-1-yl)benzyl[pyrimidine 2.0 G. of N-[α$^5$-(2,4-diamino-5-pyrimidinyl)-3-(pyrimidinyl)-3-(pyrrol-1-yl)-2,5-xylyl]-acetamide, (prepared as described in the first paragraph of Example 8) and 70 ml. of 1-N hydrochloric acid were heated on a steam bath for 3 hours. After cooling, the solution was made alkaline with potassium carbonate, the precipitate filtered off in vacuo and recrystallized from ethanol/petroleum ether. The 2,4-diamino-5-[3-amino-4-methyl-5-(pyrrol-1-yl)benzyl]pyrimidine melted at 202°-204° C.

EXAMPLE 10

Preparation of 2,4-diamino-5-[4-methoxy-3,5-di(pyrrol-1-yl)-benzyl]-pyrimidine A solution of 0.33 g. of sodium in 30 ml. of absolute ethanol was treated with 1.43 g. of guanidine hydrochloride and 1.9 g. of α-(anilinomethylene)-4-methoxy-3,5-di(pyrrol-1-yl)hydrocinnamonitrile and boiled under reflux for 20 hours. The alcohol was removed in vacuo, the residue taken up in water, filtered off under suction and recrystallized from methanol. The 2,4-diamino-5-[4-methoxy-3,5-di(pyrrol-1-yl)-benzyl]-pyrimidine melted at 182°-183° C.

The starting material was prepared as follows:

A mixture of 19.6 g. of methyl 3,5-diamino-4-methoxybenzoate, 100 ml. of glacial acetic acid and 36 g. of diethoxytetrahydrofuran was stirred for 30 minutes at 100° C. The glacial acetic acid was removed in vacuo. There was obtained from the residue, after purification over aluminum oxide with benzene and recrystallization from methanol, methyl 4-methoxy-3,5-di(pyrrol-1-yl)benzoate, having a melting point of 55°-57° C.

A suspension of 5.8 g. of sodium hydride (50% dispersion in oil) and 15 g. of dimethylsulfone in 80 ml. of dimethylsulfoxide was stirred with the exclusion of moisture for 2 hours at 50° C. Thereupon, 23.6 g. of methyl 4-methoxy-3,5-di(pyrrol-1-yl)benzoate were added and the mixture was stirred for 2 hours at room temperature. The solution was diluted with 300 ml. of water, the aqueous solution made weakly acidic with acetic acid, the precipitate filtered off under suction and recrystallized from ethanol. The 4'-methoxy-2-methylsulfonyl-3',5'-di(pyrrol-1-yl)acetophenone melted at 155°-156° C.

A suspension of 3.4 g. of 4'-methoxy-2-methylsulfonyl-3',5'-di(pyrrol-1-yl)acetophenone and 0.8 g. of sodium borohydride in 70 ml. of 90% ethanol was stirred for 16 hours at room temperature. The alcohol was removed in vacuo, the residue taken up in water, filtered of under suction and recrystallized from methanol. The 4-methoxy- α-[(methylsulfonyl)methyl[-3,5-di(pyrrol-1-yl)-benzyl alcohol melted at 185°-186° C.

A mixture of 1.8 g. of 4-methoxy- α -[(methylsulfonyl)methyl]-3,5-di-(pyrrol-1-yl)benzyl alcohol, 0.41 g. of sodium methylate and 1.1 g. of β-anilinopropionitrile in 12 ml. of dimethylsulfoxide was stirred with the exclusion of moisture for 3 hours at room temperature. The mixture was diluted with 100 ml. of water, the precipitated oil extracted with ethyl acetate, the ethyl acetate solution dried over sodium sulfate and evaporated. By purification of the residue over aluminum oxide with benzene and recrystallization from ethyl acetate/petroleum ether, there was obtained α -(anilinomethylene)-4-methoxy-3,5-di(pyrrol-1-yl)hydrocinnamonitrile, having a melting point of 152° C.

EXAMPLE 11

Preparation of 2,4-diamino-5-[3,5-bis(dimethylamino)benzyl]pyrimidine

A solution of 690 mg. of sodium in 100 ml. of absolute ethanol was treated with 5.4 g. of guanidien carbonate and 3.2 g. of α-(anilinomethylene)-3,5-bis-(dimethylamino)hydrocinnamonitrile and boiled under reflux for 20 hours. After the addition of 50 ml. of water, the alcohol was evaporated in vacuo. After standing for 1 hour at 25° C., the precipitated 2,4-diamino-5-[3,5-bis(-dimethylamino)benzyl]pyrimidine was filtered off under suction, washed with water and recrystallized from methanol/ethyl acetate; melting point: 198°-199° C.

The starting material was prepared as follows:

24.9 G. of methyl 3,5-diaminobenzoate, 75.6 g. of dimethylsulfate and 207 g. of anhydrous potassium carbonate were boiled for 20 hours in 1 liter of tetrahydrofuran under a reflux condenser while stirring and excluding moisture. After cooling, the mixture was filtered and the filtrate evaporated to dryness in vacuo. The residue was treated with 200 ml. of water and the precipitated oil extracted with 400 ml. of ethyl acetate. The ethyl acetate phases were washed with 200 ml. of water, dried over magnesium sulfate and evaporated to dryness in vacuo. The residue was chromatograhed on 500 g. of silica gel with ethyl acetate/methylene chloride (1:9), there being obtained methyl 3,5-bis(dimethylamino)benzoate, having a melting point of 86°-88° C.

A suspension of 3.6 g. of sodium hydride (50% dispersion in oil) and 9.4 g. of dimethylsulfone in 50 ml. of absolute dimethylsulfoxide was stirred with the exclusion of moisture for 2.5 hours at 50° C. and then treated with 11.1 g. of methyl 3,5-bis(dimethylamino)benzoate. The mixture was stirred for 18 hours at room temperature, diluted with 500 ml. of water and extracted with 600 ml. of ethyl acetate. The ethyl acetate phases were washed with 300 ml. of water, dried over magnesium sulfate and evaporated to dryness in vacuo. Recrystallization of the residue from ethyl acetate yielded 3',5'-bis-(dimethylamino)-2-methylsulfonylacetophenone, having a melting point of 151°-153° C.

A suspension of 7.4 g. of 3',5'-bis(dimethylamino)-2-methylsulfonylacetophenone and 3.8 g. of sodium borohydride in 100 ml. of ethanol was stirred for 20 hours at 25° C. After the addition of 50 ml. of water, the alcohol was removed in vacuo and the remaining aqueous suspension extracted with 400 ml. of ethyl acetate. The ethyl acetate phases were washed with 50 ml. of water, dired over magnesium sulfate and evaporated to dryness in vacuo. Recrystallization of the residue from ethanol gave 3,5-bis(dimethylamino)- α -[(methylsulfonyl)-methyl]-benzyl alcohol, having a melting point of 142°-143° C.

A mixture of 1.6 g. of sodium methylate, 2.3 g. of β-anilinopropionitrile and 4.3 g. of 3,5-bis(dimethylamino)- α -[(methylsulfonyl)methyl]benzyl alcohol in 20 ml. of absolute dimethylsulfoxide was stirred with the exclusion of moisture for 4 hours at 50° C. The solution was diluted with 250 ml. of water and extracted with 500 ml. of ethyl acetate. The ethyl acetate phases were washed with 100 ml. of water, dried over magnesium sulfate and evaporated to dryness in vacuo. The residue was dissolved in 20 ml. of ethanol. After standing for 20 hours at 4° C., the crystallized α -(anilinomethylene)-3,5-bis(dimethylamino)hydrocinnamonitrile was filtered off under suction, washed with ethanol and dried; melting point 128°-130° C.

EXAMPLE 12

Preparation of 2,4-diamino-5-[3,5-bis(methylamino)benzyl]pyrimidine

A solution of 4.1 g. of sodium in 600 ml. of ethanol was treated with 32.4 g. of guanidine carbonate and 17.8 g. of α-(anilinomethylene)-3,5-bis(methylamino)hydrocinnamonitrile and boiled under reflux and under nitrogen gassing for 20 hours. After the addition of 500 ml. of water, the alcohol was evaporated in vacuo. After standing for 2 hours at 25° C., the precipiated 2,4-diamino-5-[3,5-bis(methylamino)benzyl]pyrimidine was filtered off under suction, washed with water and recrystallized from methanol; melting point 209° C.

The starting material was prepared as follows:

A mixture of 134 g. of methyl 3,5-diaminobenzoate, 870 ml. of acetic anhydride and 870 ml. of absolute pyridine was stirred for 20 hours at 25° C. and subsequently evaporated to dryness in vacuo. Recrystallization of the residue from ethyl acetate yielded methyl 3,5-bis(acetamido)benzoate, having a melting point of 220°-221° C.

A suspension of 88 g. of sodium hydride (50% dispersion in oil) in 800 ml. of absolute dimethylformamide was treated with a solution of 191 g. of methyl 3,5-bis-(acetamido)benzoate in 800 ml. of absolute dimethylformamide with stirring and ice cooling. After stirring for 1 hour at 25° C., 650 g. of methyl iodide were added dropwise with ice cooling. The mixture was stirred for 50 hours at 25° C., treated with 4 liters of water and extracted six times with 5 liters of ethyl acetate each time. The ethyl acetate extract was washed with 3 liters of water, dried over magnesium sulfate and evaporated to dryness in vacuo. Recrystallization of the residue from ethyl acetate/cyclohexane gave methyl 3,5-bis(N-methylacetamido)-benzoate, having a melting point of 106° C.

A suspension of 19.2 g. of sodium hydride (50% dispersion in oil) and 56.1 g. of dimethylsulfone in 200 ml. of absolute dimethylsulfoxide was stirred with the exclusion of moisture for 3 hours at 50° C. and then treated at 25° C. with 41.8 g. of methyl 3,5-bis-(N-methylacetamido)benzoate. The mixture was stirred for 18 hours at 25° C., diluted with 2 liters of water, adjusted to pH 7 with glacial acetic acid and extracted with 9 liters of ethyl acetate. The ethyl acetate solution was washed with 3 liters of water, dried over magnesium sulfate and evaporated in vacuo. Recrystallization of the residue from ethanol yielded 3',5'-bis(methylamino)-2-methylsulfonylacetophenone, having a melting point of 144°-146° C.

A suspension of 7.6 g. of sodium borohydride and 12.8 g. of 3',5'-bis-(methylamino)-2-methylsulfonylacetophenone in 200 ml. of ethanol was stirred for 18 hours at 25° C. After the addition of 50 ml. of water, the solution was evaporated to dryness in vacuo. The residue was heated to boiling in 300 ml. of ethyl acetate. The insoluble material was separated and the filtrate evaporated to dryness in vacuo. Recrystallization of the residue from ethanol gave 3,5-bis-(methylamino)- α -[(methylsulfonyl)methyl]benzyl alcohol, having a melting point of 106° C.

A mixture of 8.6 g. of sodium methylate, 12.4 g. of β-anilinopropionitrile and 20.4 g. of 3,5-bis(methylamino)- α -[(methylsulfonyl)methyl]benzyl alcohol in 100 ml. of absolute dimethylsulfoxide was stirred for 1 hour at 50° C. and then treated with 1 liter of water. The precipitated product was extracted with 3 liters of ethyl acetate. The ethyl acetate extract was washed with 1 liter o water, dried over magnesium sulfate and evaporated in vacuo. The residue was chromatographed on 1 kg. of silica gel with methylene chloride-/ethyl acetate (3:1), there being obtained α -(anilinomethylene)-3,5-bis(methylamino)hydrocinnamonitrile as brownish-colored oil.

EXAMPLE 13

Preparation of α$^{5'}$-(2,4-diamino-5-pyrimidinyl)-N-methyl-3'-methylamino-2,5-acetoxylidide A solution of 8 g. of sodium in 300 ml. of absolute ethanol was boiled under reflux with 62 g. of guanidien carbonate and 40 g. of 5'-(3-anilino-2-cyanoallyl)-N,2'-dimethyl-3'-methylaminoacetanilide for 20 hours. After the addition of 500 ml. of water, the alcohol was evaporated in vacuo. The crystallized α$^{5'}$-(2,4-diamino-5-pyrimidinyl)-N-methyl-3'-methylamino-2,5-acetoxylidide was filtered off under suction, washed with water and recrystallized from alcohol; melting point 237° C.

The starting material was prepared as follows:

A solution of 36 g. of methyl 3,5-diamino-p-toluate, in 600 ml. of absolute pyridine, was treated dropwise with 200 ml. of acetic anhydride while stirring. After stirring for 5 hours at 25° C., the precipitated methyl 3,5-bis-(acetamido)-p-toluate was filtered off under suction, washed with 300 ml. of water and recrystallized from methanol; melting point above 260° C.

A suspension of 28.8 g. of sodium hydride (50% dispersion in oil) in 800 ml. of absolute dimethylformamide was treated portionwise with 66 g. of methyl 3,5-bis-(acetamido)-p-toluate. After stirring for 20 hours at 50° C., the mixture was cooled with ice. 105 G. of methyl iodide were added dropwise and the mixture was stirred for 20 hours at room temperature. The dimethylformamide was removed in vacuo at 60° C. and the residue treated with 500 ml. of water. The precipitated produce was extracted with 3 liters of ethyl acetate. The ethyl acetate solution was washed with 500 ml. of water, dried over magnesium sulfate and evaporated in vacuo. The residue was chromatographed on 1 kg. of silica gel with acetone, there being obtained methyl 3,5-bis(N-methylacetamido)-p-toluate, having a melting point of 163°-164° C.

A suspension of 3.8 g. of sodium hydride (50% dispersion in oil) and 11.2 g. of dimethylsulfone in 40 ml. of absolute dimethylsulfoxide was stirred for 3 hours at 50° C. After cooling to 25° C., 8.8 g. of methyl 3,5-bis(N-methylacetamido)-p-toluate were added. The mixture was stirred for 18 hours at 25° C., diluted with 500 ml. of ice water, adjusted to pH 7 with glacial acetic acid, saturated with sodium chloride and extracted with 2 liters of ethyl acetate. The ethyl acetate extract was washed with 200 ml. of water, dried over magnesium sulfate and evaporated in vacuo. The residue was recrystallized from alcohol, there being obtained N-methyl-3'-methylamino-5'-[(methylsulfonyl)acetyl]-o-acetotoluidide, having a melting point of 182° C.

A suspension of 56 g. of sodium borohydride and 116 g. of N-methyl-3'-methylamino-5'-[(methylsulfonyl)acetyl]-o-acetotoluidide in 1 liter of ethanol was stirred for 20 hours at 25° C. The solvent was evaporated in vacuo, the residue treated with 2 liters of water and extracted with 9 liters of ethyl acetate. The ethyl acetate solution was washed with 1 liter of water, dried over magnesium sulfate and evaporated in vacuo. Recrystallization of the residue from ethanol yielded 5'-[1-hydroxy-2-(methylsulfonyl)ethyl]-N,2'-dimethyl-3'-methylaminoacetanilide having a melting point of 191°-192° C.

A mixture of 27 g. of sodium methylate, 41 g. of β-anilinopropionitrile and 79.5 g. of 5'-[1-hydroxy-2-(methylsulfonyl)ethyl]-N,2'-dimethyl-3'-methylaminoacetanilide in 350 ml. of absolute dimethylsulfoxide was stirred for 1 hour at 50° C., then diluted with 2 liters of water and extracted with 6 liters of ethyl acetate. The ethyl acetate extract was washed with 1 liter of water, dried over magnesium sulfate and evaporated in vacuo. The residue was chromatographed on 2 kg. of silica gel with ethyl acetate/methylene chloride (1:1), there being obtained 5'-(3-anilino-2-cyanoallyl)-N,2'-dimethyl-3'-methylaminoacetanilide as an oil.

EXAMPLE 14

Preparation of 2,4-diamino-5-[4-tert. butyl-3,5-bis(dimethylamino)benzyl]-pyrimidine A solution of 0.53 g. of sodium in 600 ml. of absolute ethanol was treated with 2.16 g. of guanidine hydrochloride and 3.95 g. of α-(anilinomethylene)-4-tert. butyl-3,5-bis(dimethylamino)hydrocinnamonitrile and boiled under reflux for 20 hours. The ethanol was removed under reduced pressure, the residue taken up in water, the precipitated 2,4-diamino-5-[4-tert. butyl-3,5-bis(dimethylamino)benzyl]pyrimidine filtered off under suction, washed with water and recrystallized from ethanol; melting point 266°-267° C.

The starting material was prepared as follows:

20 G. of 4-tert. butyl-3,5-dinitrobenzoic acid [J. Org. Chem., 19, 87-102 (1954)] and 100 ml. of thionyl chloride were boiled under reflux for 2 hours. The excess thionyl chloride was removed in vacuo, the residue dissolved in 100 ml. of acetone, and the resulting solution added dropwise to 100 ml. of methanol while stirring. The resulting mixture was boiled under reflux for 30 minutes, the methanol distilled off, the residue dissolved in benzene, the benzene solution washed with sodium carbonate solution and then with water until neutral, dried over sodium sulfate and evaporated. After recrystallization of the residue from methanol, there was obtained methyl 4-tert.butyl-3,5-dinitrobenzoate having a melting point of 115°-117° C.

28.2 G. of methyl 4-tert. butyl-3,5-dinitrobenzoate dissolved in 200 ml. of methanol were hydrogenated under normal pressure and at room temperature in the presence of 2 g. of palladium/carbon (5%). After the uptake of the theoretical amount of hydrogen, the solution was filtered from the catalyst and evaporated. The residue was dissolved in benzene and purified over aluminum oxide, there being obtained methyl 3,5-diamino-4-tert. butylbenzoate having a melting point of 71°-73° C. after recrystallization from benzene/petroleum ether.

A mixture of 25 g. of methyl 3,5-diamino-4-tert. butylbenzoate, 50 ml. of dimethylsulfate, 155 g. of dry potassium carbonate and 750 ml. of acetone was boiled for 22 hours under reflux and while stirring. After cooling, the solution was filtered off from inorganic salts, the acetone removed in vacuo, and the residue recrystallized from methanol/water, there being obtained methyl 4-tert. butyl-3,5-bis(dimethylamino)benzoate having a melting point of 80°-82° C.

A suspension of 2.4 g. of sodium hydride (50% suspension in oil) and 7.05 g. of dimethylsulfone in 17.5 ml. of dimethylsulfoxide was stirred with the exclusion of moisture for 2 hours at 50° C. 6.9 G. of methyl 4-tert. butyl-3,5-bis(dimethylamino)benzoate were then added, and the mixture was stirred at room temperature for 1.5 hours. The solution was diluted with 150 ml. of ice water, the precipitated solid material filtered off, washed with water and recrystallized from methanol, there being obtained 4'tert. butyl-3',5'-bis-(dimethylamino)-'-methylsulfonylacetophenone having a melting point of 177°-179° C.

A suspension of 8 g. of 4'-tert. butyl-3',5'-bis(dimethylamino)-2-methylsulfonylacetophenone in 200 ml. of ethanol was stirred at 20° C. for 4 hours with a solution of 2.3 g. of sodium borohydride in 25 ml. of water. After dilution with 250 ml. of ice water, the precipitated 4-tert. butyl-3,5-bis(dimethylamino)-α-[(methylsulfonyl)methyl]benzyl alcohol was filtered off under suction and recrystallized from methanol; melting point 202°-204° C.

A mixture of 4.66 g. of 4-tert. butyl-3,5-bis(dimethylamino)-α-[(methylsulfonyl)methyl]benzyl alcohol, 1.28 g. of sodium methylate and 3.3 g. of β-anilinopropionitrile in 35 ml. of dimethylsulfoxide was stirred at room temperature under nitrogen for 60 minutes. The mixture was poured into 200 ml. of ice water, the separated oil extracted with ethyl acetate, the ethyl acetate solution dried over sodium sulfate and then evaporated. By purification of the residue over aluminum oxide with benzene and recrystallization from ethanol, there was obtained α-(anilinomethylene)-4-tert. butyl-3,5-bis(-dimethylamino)hydrocinnamonitrile having a melting point of 150° C.

EXAMPLE 15

Preparation of 2,4-diamino-5-[3,4,5-tris-(dimethylamino)benzyl]-pyrimidine

A solution of 0.53 g. of sodium in 60 ml. of absolute ethanol was treated with 2.16 g. of guanidine hydrochloride and 3.8 g. of α-(anilinomethylene)-3,4,5,-tris(-dimethylamino)hydrocinnamonitrile and boiled under reflux for 20 hours. The ethanol was removed under reduced pressure, the residue taken up in water, the precipitated 2,4-diamino-5-[3,4,5-tris(dimethylamino)-benzyl]pyrimidine filtered off under suction, washed with water and recrystallized from ethanol; melting point 203°-204° C.

The starting material was prepared as follows:

27 G. of methyl 4-dimethylamino-3,5-dinitrobenzoate [Rec. trav. chim. 73, 68 (1954)] dissolved in 300 ml. of methanol were hydrogenated under normal pressure and at room temperature in the presence of 3 g. of palladium/carbon (5%). After uptake of the theoretical amount of hydrogen, the solution was filtered off from the catalyst and evaporated. The residue, methyl 3.5-diamino-4-dimethylaminobenzoate, was characterized as the monohydrochloride; melting point 222°-223° C. (from ethanol/ether).

A mixture of 37 g. of methyl 3,5-diamino-4-dimethylaminobenzoate, 113 ml. of dimethylsulfate, 350 g. of dry potassium carbonate and 14 ml. of acetone was boiled under reflux while stirring for 18 hours. After cooling, the solution was filtered off from inorganic salts, the acetone removed in vacuo, the residue dissolved in benzene, purified over aluminum oxide and recrystallized from methanol/water, there being obtained methyl 3,4,5-tris(dimethylamino)benzoate having a melting point of 61°-63° C.

A suspension of 4.8 g. of sodium hydride (50% emulsion in oil) and 14.1 g. of dimethylsulfone in 35 ml. of dimethylsulfoxide was stirred under nitrogen and with the exclusion of moisture for 2 hours at 50° C. 13.2 G. of methyl 3,4,5-tris-(dimethylamino)benzoate were then added, and the mixture was stirred at room temperature for 1.5 hours. The solution was diluted with 300 ml. of ice water, extracted with ethyl acetate, the ethyl acetate solution dried over sodium sulfate and evaporated. The residue was treated with 30 ml. of boiling methanol, cooled and filtered under suction. By recrystallization of the solid material from ethyl acetate/petroleum ether, there was obtained 3',4',5'-tris(dimethylamino)-2-dimethylsulfonylacetophenone having a melting point of 108° C.

A suspension of 15 g. of 3',4',5'-tris(dimethylamino)-2-methylsulfonylacetophenone in 400 ml. of ethanol was treated with a solution of 4 g. of sodium borohydride in 50 ml. of water and stirred at room temperature for 7 hours. After dilution with 500 ml. of water, the precipitated 3,4,5-tris(dimethylamino)-α-[(methylsulfonyl)methyl benzyl alcohol was filtered off under suction, washed with water and recrystallized from methanol; melting point 160°-162° C.

A mixture of 8.96 g. of 3,4,5-tris(dimethylamino)-α-[(methylsulfonyl)methyl]benzyl alcohol, 2.56 g. of sodium methylate and 6.6 g. of β-anilinopropiontrile in 70 ml. of dimethylsulfoxide was stirred at room temperature under nitrogen for 50 minutes. The mixture was poured into 500 ml. of ice water, the separated oil extracted with ethyl acetate, the ethyl acetate solution dried over sodium sulfate and evaporated. By purification of the residue over aluminum oxide with benzene and recrystallization from ethanol, there was obtained α-(anilinomethyl)-3,4,5-tris(dimethylamino)hydrocinnamonitrile having a melting point of 179°-181° C.

EXAMPLE 16

Preparation of 2,4-diamino-5-[3,5-bis(dimethylamino)-4-piperidinobenzyl]pyrimidine A solution of 1.22 g. of sodium in 110 ml. of absolute ethanol was treated with 5.26 g. of guanidine hydrochloride and 7.0 g. of α-(anilinomethylene)-3,5-bis(-dimethylamino-4-piperidinohydrocinnamonitrile and boiled under nitrogen and under reflux for 24 hours. The ethanol was removed under reduced pressure, the residue taken up in water, the precipitated 2,4-diamino-5-[3,5-bis(dimethylamino)-4-piperidinobenzyl]pyrimidine filtered off under suction, washed with water and recrystallized from ethanol; melting point 216°-218° C.

The starting material was prepared as follows:

15.45 G. of methyl 3,5-dinitro-4-piperidinobenzoate [Rec. trav. chim. 73, 68 (1954)]dissolved in 200 ml. of methanol were hydrogenated under normal pressure and at room temperature in the presence of 1 g. of palladium/carbon (5%). After uptake of the theoretical amount of hydrogen, the solution was filtered off from the catalyst and evaporated. By recrystallization of the residue from ethyl acetate/petroleum ether, there was obtained methyl 3,5-diamino-4-piperidinobenzoate having a melting point 133°-134° C.

A mixture of 42 g. of methyl 3,5-diamino-4-piperidinobenzoate, 75 ml. of dimethylsulfate, 232.5 g. of dry potassium carbonate and 1125 ml. of acetone was boiled under reflux and while stirring for 20 hours. After cooling, the solution was filtered off from inorganic salts, the acetone removed in vacuo, and the residue recrystallized from methanol, there being obtained methyl 3,5-bis(dimethylamino)-4-piperidinobenzoate having a melting point of 103°-105° C.

A suspension of 2.9 g. of sodium hydride (50% emulsion in oil) and 3.7 g. of dimethylsulfone in 20 ml. of dimethylsulfoxide was stirred with the exclusion of moisture for 2 hours at 50° C. 6.1 G. of methyl 3.5-bis(-dimethylamino)-4-piperidinobenzoate were then added, and the mixture was stirred at room temperature for 2 hours. The solution was diluted with 200 ml. of ice water, the precipitated material filtered off under suction, washed with water and recrystallized from methanol, there being obtained 3',5'-bis(dimethylamino)-2-methylsulfonyl-4-piperidinoacetophenone having a melting point of 165° C.

A suspension of 8.9 g. of 3',5'-bis(dimethylamino)-2-methylsulfonyl-4'-piperidinoacetophenone in 250 ml. of ethanol was treated with a solution of 2 g. of sodium borohydride in 50 ml. of water and stirred at 20° C. for 4 hours. After dilution with 350 ml. of ice water, the precipitated 3,5-bis(dimethylamino)-α-[(methylsulfonyl)methyl]-4-piperidinobenzyl alcohol was filtered off under suction and recrystallized from ethanol; melting point 179°-180° C.

A mixture of 7.4 g. of 3,5-bis(dimethylamino)-α-[(methylsulfonyl)methyl]-4-piperidinobenzyl alcohol, 1.64 g. of sodium methylate and 4.4 g. of β-anilinopropionitrile in 40 ml. of dimethylsulfoxide was stirred for 2 hours at 50° C. under nitrogen. The mixture was poured into 250 ml. of water, the precipitated product extracted with ethyl acetate, the ethyl acetate solution dried over sodium sulfate and evaporated. By purification of the residue over aluminum oxide with benzene and recrystallization from ethyl acetate/petroleum ether, there was obtained α-(anilinomethylene)-3,5-bis(dimethylamino)-4-piperidinohydrocinnamonitrile having a melting point of 200°-202° C.

EXAMPLE 17

Preparation of 2,4-diamino-5-[4-chloro-3,5-bis(methylamino)benzyl]pyrimidine

A solution of 0.85 g. of sodium in 55 ml. of absolute ethanol was treated with 3.4 g. of guanidine hydrochloride and 3.8 g. of α-(anilinomethylene)-4-chloro-3,5-bis(methylamino)hydrocinnamonitrile and boiled under reflux and under nitrogen for 24 hours. The ethanol was removed under reduced pressure, the residue taken up in water, the precipitated 2,4-diamino-5-[4-chloro-3,5-bis(methylamino)benzly]pyrimidine filtered off under suction, washed with water and recrystallized from ethanol; melting point 230° C.

The starting material was prepared as follows:

16 G. of methyl 3,5-diamino-4-chlorobenzoate were dissolved in 100 ml. of dry pyridine and treated with 40 ml. of acetic anhydride. After standing at room temperature for 2 hours and after a further 2 hours in a refrigerator, the precipitated methyl 3,5-diacetamido-4-chlorobenzoate was filtered off under suction, washed with ethyl acetate and recrystallized from ethanol; melting point 282° C.

To a suspension of 4.4 g. of sodium hydride (50% suspension in oil) in 80 ml. of dimethylformamide was added dropwise at room temperature a solution of 21.7 g. of methyl 3,5-diacetamido-4-chlorobenzoate in 240 ml. of dimethylformamide. After 1 hour, 65.1 g. of methyl iodide were added dropwise and the resulting mixture was stirred at room temperature for 48 hours. The mixture was diluted with 100 ml. of water, the precipitated product extracted with ethyl acetate, and the ethyl acetate solution evaporated. The residue was dissolved in ethyl acetate and purified over aluminum oxide, there being obtained methyl 4-chloro-3,5-bis(N-methylacetamido)benzoate which melted at 162°–164° C. after recrystallization from ethyl acetate/petroleum ether.

A suspension of 3.8 g. of sodium hydride (50% suspension in oil) and 11.2 g of dimethylsulfone in 40 ml. of dimethylsulfoxide was stirred with the exclusion of moisture for 2 hours at 50° C. 9.4 G. of methyl 4-chloro-3,5-bis-(N-methylacetamido)benzoate were then added, and the mixture was stirred at 80° C. for 3 hours. The solution was diluted with 200 ml. of ice water, the precipitated material extracted with ethyl acetate, the ethyl acetate solution purified over aluminum oxide, evaporated and the residue recrystallized from methanol, there being obtained 4'-chloro-3',5'-bis(methylamino)-2-methylsulfonylacetophenone having a melting point of 165°–167° C.

A suspension of 1.4 g. of 4'-chloro-3',5'-bis(methylamino)-2-methylsulfonylacetophenone in 50 ml. of ethanol was treated with a solution of 0.40 g. of sodium borohydride in 10 ml. of water and stirred at 20° C. for 4 hours. The ethanol was removed under reduced pressure, the residue treated with 100 ml. of ice water, the insoluble 4-chloro-3,5-bis(methylamino)-α-[(methylsulfonyl)-methyl]benzyl alcohol filtered off under suction and recrystallized from ethanol; melting point 180°–182° C.

A mixture of 13.2 g. of 4-chloro-3,5-bis(methylamino)-α-[(methylsulfonyl)-methyl]benzyl alcohol, 3.6 g. of sodium methylate and 9.6 g. of β-anilinopropionitrile in 80 ml. of dimethylsulfoxide was stirred for 5 hours under nitrogen at 50° C. The mixture was poured into 200 ml. of ice water, the separated oil extracted with ethyl acetate, the ethyl acetate solution dried over sodium sulfate and evaporated. By purification of the residue over aluminum oxide with benzene and recrystallization from ethyl acetate/petroleum ether, there was obtained α-(anilinomethylene)-4-chloro-3,5-bis(methylamino)hydrocinnamonitrile having a melting point of 142°–147° C.

EXAMPLE 18

Preparation of α-(2,4-diamino-5-pyrimidinyl)-2',6'-bis(dimethylamino)-N-methyl-acetotoluidide A solution of 0.33 g. of sodium in 30 ml. of absolute ethanol was treated with 1.43 g. of guanidine hydrochloride and 2.2 g. of 4'-(3-anilino-2-cyanoally)-2',4'-bis(dimethylamino)-N-methylacetanilide and boiled under reflux and under nitrogen for 24 hours. The ethanol was removed under reduced pressure, the residue taken up in water and the precipitated α-(2,4-diamino-5-pyrimidinyl)-2',6'-bis(dimethylamino)-N-methyl-acetotoluidide filtered off under suction, washed with water and recrystallized from methanol; melting point 267° C.

The starting material was prepared as follows:

A suspension of methyl 4-methylamino-3,5-dinitrobenzoate in 50 ml. of acetic anhydride was treated with three drops of concentrated sulfuric acid. After a short time, the solid material dissolved completely and, after 30 minutes, the product began to crystallize. The product was filtered off under suction and recrystallized from methanol. The methyl 4-(N-methylacetamido)-3,5-dinitrobenzoate melted at 156°–157° C.

9.7 G. of methyl 4-(N-methylacetamido)-3,5-dinitrobenzoate in 100 ml. of methanol were hydrogenated under normal pressure and at room temperature in the presence of 1 g. of palladium/carbon. After uptake of the theoretical amount of hydrogen, the solution was filtered off from the catalyst and evaporated. The residue was recrystallized from methanol, there being obtained methyl 3,5-diamino-4-(N-methylacetamido)-benzoate having a melting point of 221°–222° C.

A mixture of 50 g. of methyl 3,5-diamino-4-(N-methylacetamido)benzoate, 720 g. of dry sodium carbonate, 1500 ml. of acetone and 212 g. of dimethylsulfate was boiled under reflux while stirring for 24 hours. After cooling, the solution was filtered off from inorganic salts, the acetone evaporated in vacuo and methyl 3,5-bis(dimethylamino)-4-(N-methylacetamido)benzoate having a melting point of 120° C. extracted from the residue by boiling with high-boiling petroleum ether.

A suspension of 0.77 g. of sodium hydride (50% suspension in oil) and 2.28 g. of dimethylsulfone in 28 ml. of dimethylsulfoxide was stirred with the exclusion of moisture and under nitrogen for 2 hours at 50° C. 2 G. of methyl 3,5-bis(dimethylamino)-4-(N-methylacetamido)benzoate were then added, the mixture heated to 70° C. for a short time and stirred for a further 2 hours without heating. The solution was diluted with 100 ml. of ice water, washed with 100 ml. of low-boiling petroleum ether, the product extracted with ethyl acetate, the ethyl acetate solution dried over sodium sulfate and evaporated. After purification of the residue over aluminum oxide with benzene and recrystallization from ethyl acetate/petroleum ether, there was obtained 2',6'-bis(dimethylamino)-N-methyl-4'-[(methylsulfonyl)acetyl]acetanilide having a melting point of 130° C.

A suspension of 1.4 g. of 2',6'-bis(dimethylamino)-N-methyl-4'-[(methylsulfonyl)acetyl]acetanilide in 50 ml. of ethanol was treated with a solution of 0.4 g. of sodium borohydride in 10 ml. of water and stirred at room temperature for 4 hours. The ethanol was removed in vacuo, the residue treated with water, the precipitated 2',6'-bis(dimethylamino)-4'-[1-hydroxy-2-(methylsulfonyl)ethyl]-N-methylacetanilide filtered off under suction and recrystallized from ethyl acetate/petroleum ether; melting point 120° C.

A mixture of 1.23 g. of sodium methylate, 5.31 g. of 2',6'-bis(dimethylamino)-4'-[1-hyroxy-2-(methylsulfonyl)ethyl]N-methylacetanilide and 3.3 g. of β-anilinopropionitrile in 40 ml. of dimethylsulfoxide was stirred at room temperature under nitrogen for 5 hours. The mixture was poured into 200 ml. of ice water, the separated oil extracted with ethyl acetate, the ethyl acetate solution dried over sodium sulfate and evaporated. After purification of the residue over aluminum oxide with benzene and recrystallization from ethyl acetate/petroleum ether, there was obtained 4'-(3-anilino-2-cyanoallyl)-2',6'-bis(dimethylamino)-N-methylacetanilide having a melting point of 190°–200° C.

EXAMPLE 19

Preparation of 2,4-diamino-5-[3,5-bis(dimethylamino)-4-piperidinobenzyl-pyrimidine 4,6 g. of 3,5-bis(dimethylamino)-4-piperidinobenzaldehyde and 17 g. of βmethoxypropionitrile were added to a solution of 0.2 g. of sodium in 10 ml. of absolute methanol and the mixture was boiled under reflux for 3 hours. Then, a solution of 1.23 g. of sodium and 5.15 g. of guanidine hydrochloride was prepared, filtered and added to the mixture. The resulting mixture was boiled under reflux for 24 hours, whereby approximately half of the methanol was distilled off. After cooling, the precipitated 2,4-diamino-5[3,5-bis(dimethylamino)-4-piperidinobenzyl]pyrimidine was filtered off under suction, washed with water and recrystallized from ethanol; melting point 216°–218° C.

The starting material was prepared as follows:

A solution of 25g. of methyl 3,5-bis(dimethylamino)-4-piperidinobenzoate in 150 ml. of absolute tetrahydrofuran was added dropwise to a solution of lithium aluminum hydride in 300 ml. of absolute tetrahydrofuran, and the mixture was boiled under reflux for 3 hours. After cooling, the excess lithium aluminum hydride was cautiously decomposed with 100 ml. of ethyl acetate and then with 3 ml. of water and the sodium evaporated to dryness. The residue was taken up in water, the oily product extracted with ethyl acetate and the ethyl acetate solution dried and evaporated. After recrystallization from high-boiling petroleum ether, there was obtained 3,5-bis(dimethylamino)-4-piperidinobenzyl alcohol having a melting point of 90°–92° C.

12.9 G. of 3,5-bis(dimethylamino)-4-piperidinobenzyl alcohol, 17.1 g. of activated manganese dioxide and 80 ml. of chloroform were mixed together and stirred at room temperature for 48 hours. The manganese dioxide was filtered off, washed with chloroform and the chloroform evaporated. After purification over aluminum oxide with benzene and recrystallization from ethanol, there was obtained 3,5-bis(dimethylamino)-4-piperidinobenzaldehyde having a melting point of 114°–116° C.

The following Example illustrates a typical pharmaceutical preparation containing one of the benzylpyrimidine derivatives provided by the present invention:

EXAMPLE A

Tablets of the following composition are prepared:

| | Per Tablet |
|---|---|
| 2,4-Diamino-5-(4-chloro-3-dimethylamino-5-methylaminobenzyl)pyrimidine | 60 mg. |
| Sulfamethoxazole | 225 mg. |
| Maize Starch | 100 mg. |
| Talc | 15 mg. |
| Magnesium Stearate | 5 mg. |
| Lactose | 233 mg. |
| Gelatin | 12 mg. |
| Total Weight | 650 mg. |

We claim:

1. A compound of the formula

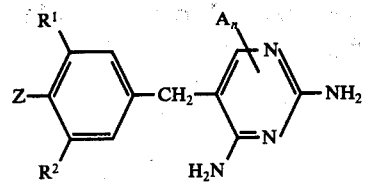

wherein $R^1$ and $R^2$ each, independently, is amino, pyrrolo, pyrrolidino, piperidino, $C_{1-3}$-alkyl-substituted pyrrolo, $C_{1-3}$-alkyl-substituted pyrrolidino, $C_{1-3}$-alkyl-substituted piperidino, -NHR$^3$, -N(R$^3$)$_2$, -NHR$^4$, -N(R$^3$)(R$^4$), -NR$^3$COOR$^3$, -NHCOOR$^3$, -NHCONHR$^3$, -NHCONH$_2$ or -N(NO)R$^3$ wherein $R^3$ is $C_{1-4}$-alkyl or $C_{2-4}$-alkenyl, $R^4$ is formyl, acetyl, propionyl, butyryl, ethoxyacetyl or mesyl; Z is hydrogen, chlorine, bromine, pyrrolo, pyrrolidino, piperidino or morpholino or $R^3$, OR$^3$ or -N(R$^3$)$_2$; A is an oxygen atom bonded to one of the cyclic nitrogen atoms; and $n$ is 0 or 1, or a pharmaceutically acceptable acid addition salt thereof.

2. A compound in accordance with claim 1, wherein $R^1$ and $R^2$ each, independently, is amino, pyrrolo, pyrrolidino, piperidino, -NHR$^3$ or -N(R$^3$)$_2$, wherein $R^3$ is $C_{1-4}$-alkyl or $C_{2-4}$-alkenyl and Z is chlorine or bromine or the group $R^3$ or OR$^3$.

3. A compound in accordance with claim 2, wherein $n$ is 0.

4. A compound in accordance with claim 1,2,4-diamino-5-[3,5-bis(dimethylamino)-4-methylbenzyl]-pyrimidine.

5. A compound in accordance with claim 1, 5'-[2,4-diamino-5-pyrimidinyl)methyl]-3'-dimethylamino-2'-methoxy-N-methylacentanilide.

6. A compound in accordance with claim 1, 2,4-diamino-5(3-dimethylamino-4-methoxy-5-methylaminobenzyl)pyrimidine.

7. A compound in accordance with claim 1, 2,4-diamino-5-[3,5-bis(dimethylamino)-4-methoxybenzyl]-pyrimidine.

8. A compound in accordance with claim 1, 2,4-diamino-5[4-chloro-3,5-bis(dimethylamino)benzyl]-pyrimidine.

9. A compound in accordance with claim 1 2,4-diamino-5-(4-chloro-3-dimethylamino-5-methylaminobenzyl)pyrimidine.

10. A compound in accordance with claim 1, 2,4-diamino-5-[3,5-bis(2,5-dimethylpyrrol-1-yl)-4-methylbenzyl]pyrimidine.

11. A compound in accordance with claim 1, N-[α$^5$-(2,4-diamino-5-pyrimidinyl)-3-(pyrrol-1-yl)-2,5-xylyl]-acetamide.

12. A compound in accordance with claim 1, 2,4-diamino-5[3-amino-4-methyl-5-(pyrrol-1yl)benzyl]pyrimidine.

13. A compound in accordance with claim 1, 2,4-diamino-5[4-methoxy-3,5-di(pyrrol-1-yl)benzyl]pyrimidine.

14. A compound in accordance with claim 1, 2,4-diamino-5[3,5-bis(dimethylamino)benzyl]pyriminidine.

15. A compound in accordance with claim 1, 2,4-diamino-5-[3,5-bis-(methylamino)benzyl]pyrimidine.

16. A compound in accordance with claim 1, $\alpha^{5'}$-(2,4-diamino-5-pyrimidinyl)-N-methyl-3'-methylamino-2,5-acetoxylidide.

17. A compound in accordance with claim 1, 2,4-diamino-5[4-tert. butyl-3,5-bis(dimethylamino)benzyl]pyrimidine.

18. A compound in accordance with claim 1, 2,4-diamino-5-[3,4,5-tris-(dimethylamino)benzyl]pyrimidine.

19. A compound in accordance with claim 1, 2,4-diamino-5-[3,5-bis-(dimethylamino)-4-piperidinobenzyl]pyrimidine.

20. A compound in accordance with claim 1, 2,4-diamino-5-[4-chloro-3,5-bis(methylamino)benzyl]pyrimidine.

21. A compound in accordance with claim 1, $\alpha$-(2,4-diamino-5-pyrimidinyl)-2',6'-bis(dimethylamino)-N-methylacetotoluidide.

* * * * *

UNITED STATES PATENT AND TRADEMARK OFFICE
CERTIFICATE OF CORRECTION

PATENT NO. : 4,039,543
DATED : August 2, 1977
INVENTOR(S) : Ivan Kompis et al.

It is certified that error appears in the above-identified patent and that said Letters Patent are hereby corrected as shown below:

Column 26, claim 5, line 48, "5'-[2,4-" should be:

5'-[(2,4-

Column 26, claim 6, line 52, "diamino-5(3-" should be:

diamino-5-(3-

Column 26, claim 8, line 58, "diamino-5[4-" should be:

diamino-5-[4-

Column 27, claim 12, line 2, "5-(pyrrol-lyl) should be:

5-(pyrrol-1-yl)

UNITED STATES PATENT AND TRADEMARK OFFICE
CERTIFICATE OF CORRECTION

PATENT NO. : 4,039,543
DATED : August 2, 1977
INVENTOR(S) : Ivan Kompis et al.

It is certified that error appears in the above-identified patent and that said Letters Patent are hereby corrected as shown below:

Column 27, claim 13, line 6, "diamino-5[4-" should be:

diamino-5-[4-

Column 27, claim 14, line 10, "diamino-5[3,5-" should be:

diamino-5-[3,5-

Column 28, claim 17, line 2, "diamino-5[4-tert." should be:

diamino-5-[4-tert.

Signed and Sealed this

*Twenty-second* Day of *November 1977*

[SEAL]

*Attest:*

RUTH C. MASON
*Attesting Officer*

LUTRELLE F. PARKER
*Acting Commissioner of Patents and Trademarks*